US00PP09214P

United States Patent [19]

Trees

[11] Patent Number: Plant 9,214

[45] Date of Patent: Jul. 25, 1995

[54] NEW GUINEA IMPATIENS NAMED BFP-364 DEEP CORAL

[75] Inventor: Scott C. Trees, Arroyo Grande, Calif.

[73] Assignee: Geo. J. Ball, Inc., West Chicago, Ill.

[21] Appl. No.: 338,162

[22] Filed: Nov. 8, 1994

[51] Int. Cl.[6] ..... A01H 5/00

[52] U.S. Cl. ..... Plt./87.6

[58] Field of Search ..... Plt. 87.6

[56] References Cited

U.S. PATENT DOCUMENTS

P.P. 7,837 3/1992 Kientzler ..... Plt./87.6

*Primary Examiner*—James R. Feyrer

*Attorney, Agent, or Firm*—Burns, Doane, Swecker & Mathis

[57] ABSTRACT

A new and distinct New Guinea Impatiens cultivar named BFP-364 Deep Coral is provided. This new cultivar was the result of a controlled breeding program wherein the BSR-195 Salmon cultivar U.S. Plant Pat. No. 8,870) was pollinated by a plant designated 3617-10 (non-patented in the United States). The new cultivar forms attractive large dark coral flowers displaying an iridescent appearance, variegated bronze foliage, a strong basal branching character, and a medium upright growth habit. The new cultivar can be readily distinguished from the Melissa cultivar U.S. Plant Pat. No. 7,837).

1 Drawing Sheet

SUMMARY OF THE INVENTION

The present invention comprises a new and distinctive Impatiens plant, botanically known as New Guinea Impatiens, and hereinafter referred to by the cultivar name BFP-364 Deep Coral.

The new cultivar is the product of a planned breeding program. More specifically, the breeding program which resulted in the production of the new cultivar was carried out in a controlled environment during 1992 at Arroyo Grande, Calif., U.S.A. The female parent (i.e., the seed parent) was the BSR-195 Salmon cultivar (U.S. Plant Pat. No. 8,870) which exhibits large medium salmon flowers with medium green foliage. The male parent (i.e., the pollen parent) was plant designated 3617-10 (non-patented in the United States) which exhibits large red flowers with dark bronze foliage. The parentage of the new cultivar can be summarized as follows:

BSR-195 Salmon×3617-10

The seeds resulting from the above pollination were sown and plantlets were obtained which were physically and biologically different from each other. Selective study resulted in the identification of a single plant of the new cultivar. This plant had large coral flowers and initially was designated BFP-364.

It was found that the new cultivar of the present invention:

(a) exhibits attractive large deep coral flowers,
(b) forms bronze foliage with variegation under high light conditions,
(c) exhibits a good branching character, and
(d) exhibits a medium upright growth habit.

Asexual reproduction of the new cultivar by terminal or stem cuttings taken during 1993, at Arroyo Grande, Calif., U.S.A. has demonstrated that the characteristics of the new cultivar as herein described are firmly fixed and are retained through successive generations of such asexual propagation.

The BFP-364 Deep Coral cultivar has not been observed under all possible environmental conditions to date. Accordingly, it is possible that the phenotype may vary somewhat with variations in the environment, such as temperature, light intensity, and day length.

When the new cultivar of the present invention is compared to the Melissa cultivar (U.S. Plant Pat. No. 7,837) it is found that the new variety exhibits larger flowers and displays bronze variegated foliage whereas the foliage of the Melissa cultivar is solid dark green.

When plant material of the BFP-364 Deep Coral cultivar is subjected to standard random amplified polymorphic DNA marker analysis (RAPD) using polymerase chain reaction (PCR) and a known unique set of DNA primers, it is found to exhibit a different fingerprint map when compared to that of Melissa cultivar which confirms its genetic distinctiveness.

Plants of the new cultivar will be marketed under the Celebration trademark by Geo. J. Ball, Inc.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at West Chicago, Ill. U.S.A.

DETAILED DESCRIPTION

The chart used in the identification of colors described herein is the R.H.S. Colour Chart of The Royal Horticultural Society, London, England. The color values were determined during the third week of July, 1994. The readings were taken between 9:00 and 10:00 a.m. under 2,000 footcandles of light at West Chicago, Ill., U.S.A. The plants were produced from cuttings taken from stock plants and were grown under greenhouse conditions comparable to those used in commercial practice while utilizing a soiless growth medium and maintaining temperatures of approximately 72° F.

during the day and approximately 65° F. during the night.

Propagation:

*Type cutting.*—Terminal tip.

*Time to initiate roots.*—Approximately 14 to 21 days with the shorter times generally being experienced in the summer and the longer times in the winter.

*Rooting habit.*—Fibrous, and branching.

Plant description:

*Form.*—Strong basal branching.

*Habit of growth.*—Medium upright mounded. A mature plant commonly measures approximately 20 to 23 cm. in height and approximately 30 to 35 cm. in width compared to approximately 19 to 24 cm. in height and approximately 25 to 30 cm. in width for the Melissa cultivar.

*Foliage.*—The configuration is narrow and lanceolate. The leaves of the new cultivar commonly measure approximately 11.3 to 13.5 cm. in length and approximately 3.7 to 4.0 cm. in width while those of the Melissa cultivar commonly measure approximately 7.0 to 9.0 cm. in length and approximately 2.5 to 3.5 cm. in width. The foliage of the new cultivar is Greyed-Purple Group 187A with mid-rib of Red Group 45B (adaxial) and Greyed-Purple Group 187C (abaxial). Under high light conditions the new cultivar exhibits foliage of 187A at the margins with variegation along mid-rib of Yellow-Orange Group 19A (adaxial) and Greyed-Purple Group 187C (abaxial). This can be compared to Green Group 139A (adaxial) and Greyed-Purple Group 187B (abaxial) for the Melissa cultivar. The stem color is Green Group 187D for both the BFP-364 Deep Coral and Melissa cultivars.

Flower description

*Flowering habit.*—Freely flowering.

*Natural flowering season.*—Throughout the year in a greenhouse environment.

*Flowers borne.*—Above the foliage arising from leaf axils.

*Flower color.*—Red Group 50A (adaxial) and Red Group 50B (abaxial). This can be compared to Red Group 52A with attachment points of Red Group 52B (adaxial) and Red Group 52B (abaxial) for the Melissa cultivar.

*Quantity of flowers.*—Approximately 8 to 10 per branch compared to 10 to 12 per branch for the Melissa cultivar.

*Number of petals.*—Five.

*Flower size.*—Approximately 6.0 to 6.5 cm. in length and approximately 6.0 to 6.5 cm. in length. This can be compared to a length of approximately 5.8 to 6.1 cm. and a width of approximately 5.8 to 6.1 cm. for the Melissa cultivar.

*Nectary length.*—Approximately 5.9 cm. which can be compared to approximately 5.5 cm. for the Melissa cultivar.

*Nectary color.*—Red Group 53C which can be compared to Red Group 53B for the Melissa cultivar.

*Reproductive organs.*—The anthers are fused together forming one organ that surrounds the pistil. Generally the anthers shed pollen prior to the stigma becoming receptive. The pollen color is Yellow-Orange Group 19B for the new cultivar and Yellow-Orange Group 22D for the Melissa cultivar. The stigma color is Red-Purple Group 59B and can be compared with Red-Purple Group 59A for the Melissa cultivar. The ovary color is Yellow-Green Group 144B which can be compared to Green Group 137D for the Melissa cultivar.

I claim:

1. A new and distinct cultivar of New Guinea Impatiens named BFP-364 Deep Coral substantially as herein shown and described, which:

(a) exhibits attractive large deep coral flowers,
(b) forms bronze foliage with variegation under high light conditions,
(c) exhibits a good branching character, and
(d) exhibits a medium upright growth habit.

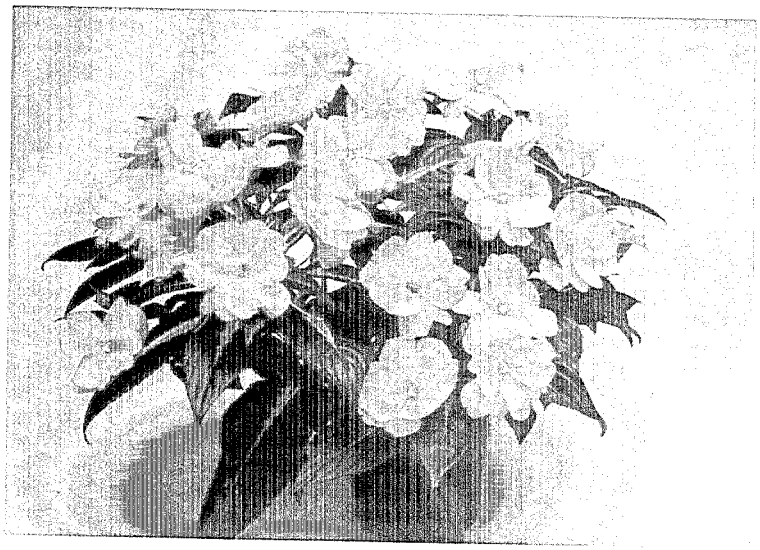

* * * * *